United States Patent [19]
Seymour

[11] Patent Number: 5,189,037
[45] Date of Patent: Feb. 23, 1993

[54] SYNERGISTIC COMBINATIONS IN THE TREATMENT OF ANXIETY

[75] Inventor: Patricia A. Seymour, Mystic, Conn.

[73] Assignee: Pfizer Inc, New York, N.Y.

[21] Appl. No.: 862,392

[22] Filed: Apr. 2, 1992

Related U.S. Application Data

[62] Division of Ser. No. 690,412, Apr. 23, 1991, Pat. No. 5,124,346.

[51] Int. Cl.$^5$ ................ A61K 31/135; A61K 31/495; A61K 31/50
[52] U.S. Cl. .................................... 514/252; 514/657
[58] Field of Search ................ 514/252, 657

[56] References Cited

PUBLICATIONS

Soderpalm et al., J. Neural. Transm., vol. 76, pp. 191–204 (1989).
Gower et al., Eur. J. Pharmacol., vol. 155, pp. 129–137 (1988).
Engel et al., Eur. J. Pharmacol., vol. 105, pp. 365–368 (1984).

Primary Examiner—Frederick E. Waddell
Assistant Examiner—Raymond J. Henley, III
Attorney, Agent, or Firm—Peter C. Richardson; J. Trevor Lumb; Gregg C. Benson

[57] ABSTRACT

Combinations having synergistic anxiolytic activity which comprise a first component selected from the group consisting of 8-hydroxy-2-(dipropylamino)-1,2,3,4-tetrahydronaphthalene, gepirone, ipsapirone, tandospirone, (7S,9S)-2-(2-pyrimidyl)-7-(succinimidomethyl)-perhydro-1H-pyrido[1,2-a]pyrazine, or chlordiazepoxide; and a second component selected from the group consisting of 1-(2-pyrimidyl)pyrazine and idazoxan.

5 Claims, No Drawings

SYNERGISTIC COMBINATIONS IN THE TREATMENT OF ANXIETY

This is a division, of application Ser. No. 07/690,412, filed on Apr. 23, 1991.

BACKGROUND OF THE INVENTION

The present invention is directed to synergistic, anxiolytic combinations of one of 8-hydroxy-2-(dipropylamino)-1,2,3,4-tetrahydronaphthalene, gepirone, ipsapirone, tandospirone, (7S,9S)-2-(2-pyrimidyl)-7-(succinimidomethyl)-perhydro-1H-pyrido[1,2-a]pyrazine, or chlordiazepoxide; with either 1-(2-pyrimidyl)-piperazine or idazoxan.

It is well established that Vogel's so-called anticonflict test or drinking conflict test is a specific and reliable model for the detection of drugs having anxiolytic activity (for example, see Soderpalm et al., J. Neural Transm., v. 16, pp. 191-204, 1989, at page 192). Compounds which have been reported to possess activity in this test include said 8-hydroxy-2-(dipropylamino)-1,2,3,4-tetrahydronaphthalene (Engel et al., European J. Pharmacol., v. 105, pp. 365-368, 1984; no significant activity noted under the conditions used in present studies); gepirone, having the formula

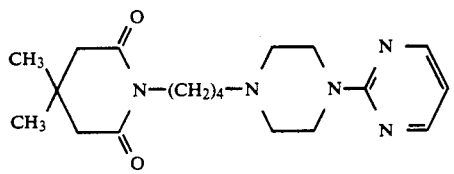

(Temple Jr., U.S. Pat. No. 4,423,049; activity confirmed in present studies); ipsapirone, having the formula

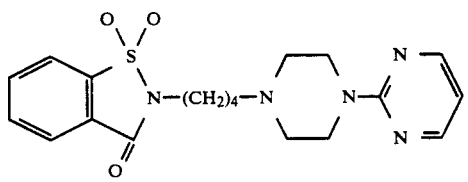

(Dompert et al., German patent publication 3,321,969-A1; activity confirmed in present studies); tandospirone, having the formula

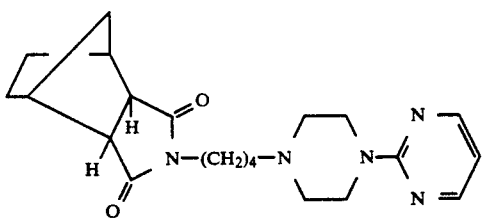

(Ishizumi et al., U.S. Pat. No. 4,507,303; also known as SM-3997; activity confirmed in present studies); (7S,9S)-2-(2-pyrimidyl)-7-(succinimidomethyl)perhydro-1H-pyrido[1,2-a]pyrazine (Bright et al., published International Patent Application No. WO 90/08147; also known as CP-93,393; activity confirmed in present studies); chlordiazepoxide (Soderpalm et al., cited above; activity confirmed in present studies; idazoxan (racemic-2-(1,4-benzodioxan-2-yl)-2-imidazoline;

Gower et al., European J. Pharmacol., v. 155, pp. 129-137, 1988; activity confirmed in present studies); and 1-(2-pyrimidyl)piperazine (Gower et al., loc. cit.; activity confirmed in present studies).

Gower et al., loc. cit., have reported buspirone (an anxiolytic agent structurally related to above gepirone, ipsapirone and tandospirone) in combination with idazoxan shows a simple additive effect in the Vogel anticonflict test. Soderpalm et al., loc. cit., have reported that, after coadministration of idazoxan, rats treated with alprazolam or diazepam (benzodiazepines structurally related to present chlordiazepoxide) accepted significantly more shocks in the Vogel anti-conflict test.

SUMMARY OF THE INVENTION

The present invention is directed to drug combinations which show synergistic activity in the Vogel anticonflict test, which as noted above, is of well-established value as a predictor of antianxiety utility in mammals, including man. In particular, the present invention is directed to a synergistic combination comprising a first component which is:

8-hydroxy-2-(dipropylamino)-1,2,3,4-tetrahydronaphthalene
gepirone,
ipsapirone,
tandospirone,
(7S,9S)-2-(2-pyrimidyl)-7-(succinimidomethyl)-perhydro-1H-pyrido[1,2-a]pyrazine, or
chlordiazepoxide;

and a second component which is:

1-(2-pyrimidyl)piperazine, or
idazoxan;

for use in the treatment of anxiety.

Based upon their pronounced synergistic effect, the combination of 8-hydroxy-2-(dipropylamino)-1,2,3,4-tetrahydronaphthalene with either 1-(2-pyrimidyl)piperazine or idazoxan; and the combination of gepirone, ipsapirone, tandospirone, (7S,9S)-2-(2-pyrimidyl)-7-(succinimido-methyl)perhydro-1H-pyrido[1,2-a]pyrazine or chlordiazepoxide with idazoxan are of particular value in said treatment.

The present invention is also directed to pharmaceutical compositions comprising said combinations, and to a method treating anxiety with said combinations.

DETAILED DESCRIPTION OF THE INVENTION

The present invention is readily carried out. The individual compounds of the present combinations are known, and available commercially or by known synthetic methods.

The anxiolytic activity of the compounds combined according to the present invention is demonstrated and measured using a variation of the Vogel anti-conflict test. See Vogel et al., Psychopharmacologia, 21, 1 (1971). In this test, groups of rats (generally 8-10 in number) are deprived of water for 48 hours, and then presented an opportunity to drink water from an electrified spout. After a brief period of exposure to the test chamber and unpunished drinking, the number of times that the rats drink water (and therefore also receive an electric shock) during a 10 minute test period is measured for control rats and for rats which have been previously dosed with a test compound or compounds (treated rats). An increase in the number of times that treated rats drink water, over the number of times that control rats drink water, is indicative of antianxiety activity in the compound or combination of compounds being tested.

The compounds are dosed alone or in combination by any conventional route, e.g., p.o., i.p., s.c. or i.m. The animals are generally dosed 15-60 minutes prior to initiation of the 10 minute test period. When dosed separately, the compounds of the combination can be dosed at the same time or at different times, and by the same route of administration or by different routes.

For use in alleviating the symptoms of anxiety in a human subject, a combination of the present invention is administered in an antianxiety amount, in single or divided daily doses. In a typical human weighing 50-70 kg, the daily dosage (in single or divided doses) of the first component will range as follows:

| | |
|---|---|
| 8-hydroxy-2-(dipropylamino)-1,2,3,4-tetrahydronaphthalene | 1-50 mg |
| gepirone | 2-100 mg |
| ipsapirone | 2-100 mg |
| tandospirone | 2-100 mg |
| (7S,9S)-2-(2-pyrimidyl)-7-(succinimidomethyl)-perhydro-1H-pyrido[1,2-a]pyrazine | 2-100 mg |
| chlordiazepam | 5-50 mg; | and of the second component will range as follows:

| | |
|---|---|
| idazoxan | 1 to 50 mg |
| 1-(2-pyrimidyl)piperazine | 2 to 100 mg. |

At the same time, the weight ratio of first and second components will generally range from 1 to 10 to 10 to 1, respectively. Of course, depending on the needs of the patient, dosage outside of the specified ranges will be administered at the discretion of the attending physician.

The preferred route of administration is generally oral, but parenteral administration (e.g., intramuscular, intravenous, intradermal) will be preferred in special cases, e.g., where oral absorption is impaired as by disease, or the patient is unable to swallow. The first and second components can be administered as a mixture as a single unit dosage; or separately, in individual dosage units. In the latter case, although not essential, the route of administration will generally be the same (e.g., both oral or both i.m.).

The compounds of the present invention are generally administered in the form of pharmaceutical compositions, comprising one or both of the components, together with a pharmaceutically acceptable vehicle or diluent. Such compositions are generally formulated in a conventional manner utilizing solid or liquid vehicles or diluents as appropriate to the mode of administration: for oral administration, in the form of tablets, hard or soft gelatin capsules, suspensions, granules, powders and the like; and, for parenteral administration, in the form of injectable solutions or suspensions, and the like.

The present invention is illustrated by the following examples, but is not limited to the details thereof.

EXAMPLE 1

Activity of 8-Hydroxy-2-(dipropylamino)-1,2,3,4-tetrahydronaphthalene (DPAT) and Idazoxan (IDZ), Alone and In Combination, in the Vogel Anticonflict Test in Rats According to the method detailed in the specification above, DPAT and IDZ were tested in the Vogel anticonflict test with results as follows:

| Dose of IDZ SC, 60 min. prior to test (mg/kg) | Dose of DPAT SC, 30 min. prior to test (mg/kg) | Number of Drinks over 10 min. Test Period | Observed Increase in No. of Drinks over Control | Calculated Increase in No. of Drinks if Additive |
|---|---|---|---|---|
| TEST A | | | | |
| 0 | 0 | 10.8 | — | — |
| | 0.178 | 9.5 | −1.3 | — |
| | 0.56 | 5.9 | −4.9 | — |
| 0.56 | 0 | 10.4 | −0.4 | — |
| | 0.178 | 60.0 | +49.2** | −1.7 |
| | 0.56 | 42.0 | +31.2** | −5.3 |
| 1.78 | 0 | 20.0 | +9.2 | — |
| | 0.178 | 64.0 | +53.2** | +8.3 |
| | 0.56 | 17.0 | +6.2* | +4.7 |
| Test B | | | | |
| 0 | 0 | 7.5 | — | — |
| | 0.178 | 13.9 | +6.4 | — |
| | 0.56 | 7.3 | −0.2 | — |
| 0.56 | 0 | 10.8 | +3.3 | — |
| | 0.178 | 41.0 | +33.5** | 9.9 |
| | 0.56 | 30.0 | +22.5** | 3.1 |
| 1.78 | 0 | 16.9 | 9.4 | — |
| | 0.178 | 64.9 | 57.4** | 15.8 |
| | 0.56 | 33.1 | 25.6** | 9.2 |
| Test C | | | | |
| 0 | 0 | 9.3 | — | — |
| | 0.178 | 11.3 | +2.0 | — |
| 0.56 | 0 | 11.3 | +2.0 | — |
| | 0.178 | 87.6 | +78.3** | +4.0 |
| 1.78 | 0 | 24.8 | +15.5 | — |
| | 0.178 | 115.4 | +106.8** | +17.5 |

*Greater than additive; synergism indicated
**Much greater than additive; pronounced synergism

EXAMPLE 2

Activity of 8-Hydroxy-2-(dipropylamino)-1,2,3,4-tetrahydronaphthalene (DPAT) and 1-(2-pyrimidyl)piperazine (1-PP), Alone and In Combination, in the Vogel Anticonflict Test in Rats According to the method detailed in the specification above, DPAT and 1-PP were tested in the Vogel anticonflict test with results as follows:

| Dose of 1-PP SC, 30 min. prior to test (mg/kg) | Dose of DPAT SC, 30 min. prior to test (mg/kg) | Number of Drinks over 10 min. Test Period | Observed Increase in No. of Drinks over Control | Calculated Increase in No. of Drinks if Additive |
|---|---|---|---|---|
| Test A | | | | |
| 0 | 0 | 10.0 | — | — |
| | 0.178 | 10.5 | +0.5 | — |
| | 0.56 | 7.1 | −2.9 | — |
| 1.78 | 0 | 8.0 | −2.0 | — |
| | 0.178 | 10.6 | +0.6 | −1.5 |
| | 0.56 | 47.4 | +37.4** | −4.9 |
| 5.6 | 0 | 19.8 | +9.8 | — |
| | 0.178 | 31.3 | +21.3** | +10.3 |
| | 0.56 | 28.4 | +18.4* | +6.9 |
| Test B | | | | |

-continued

| Dose of 1-PP SC, 30 min. prior to test (mg/kg) | Dose of DPAT SC, 30 min. prior to test (mg/kg) | Number of Drinks over 10 min. Test Period | Observed Increase in No. of Drinks over Control | Calculated Increase in No. of Drinks if Additive |
|---|---|---|---|---|
| 0 | 0 | 5.5 | — | — |
|  | 0.178 | 8.4 | +2.9 | — |
|  | 0.56 | 5.1 | −0.4 | — |
| 0.56 | 0 | 25.4 | +19.9 | — |
|  | 0.178 | 42.8 | +37.3** | +22.8 |
|  | 0.56 | 27.1 | +21.6* | +19.5 |
| 10.0 | 0 | 47.8 | +42.3 | — |
|  | 0.178 | 41.3 | +35.8 | +45.2 |
|  | 0.56 | 32.3 | +26.8 | +41.9 |

*Greater than additive; synergism indicated
**Much greater than additive; pronounced synergism

EXAMPLE 3

Activity of Tandosperone (TSP) and Idazoxan (IDZ), Alone and in Combination, in the Vogel Anticonflict Test in Rats According to the method detailed in the specification above, TSP and IDZ were tested in the Vogel anticonflict test with results as follows:

| Dose of IDZ SC, 60 min. prior to test (mg/kg) | Dose of TSP ip, 15 min. prior to test (mg/kg) | Number of Drinks over 10 min. Test Period | Observed Increase in No. of Drinks over Control | Calculated Increase in No. of Drinks if Additive |
|---|---|---|---|---|
| Test A |  |  |  |  |
| 0 | 0 | 15.1 | — | — |
|  | 1.78 | 20.5 | +5.4 | — |
|  | 5.6 | 32.9 | +17.8 | — |
| 0.56 | 0 | 15.8 | +0.7 | — |
|  | 1.78 | 47.3 | +32.2** | +6.1 |
|  | 5.6 | 49.1 | +34.0** | +18.5 |
| 1.78 | 0 | 26.4 | +11.3 | — |
|  | 1.78 | 42.1 | +27.0** | +16.7 |
|  | 5.6 | 70.3 | +55.2** | +29.1 |
| Test B |  |  |  |  |
| 0 | 0 | 10.8 | — | — |
|  | 0.32 | 15.8 | +5.0 | — |
|  | 1.0 | 13.4 | +2.6 | — |
| 0.32 | 0 | 15.0 | +4.2 | — |
|  | 0.32 | 23.1 | +12.3* | +9.2 |
|  | 1.0 | 32.6 | +21.8* | +6.8 |
| 1.0 | 0 | 12.4 | +1.6 | — |
|  | 0.32 | 7.0 | −3.8 | +6.6 |
|  | 1.0 | 26.3 | +15.5* | +4.2 |
| Test C |  |  |  |  |
| 0 | 0 | 6.5 | — | — |
|  | 1.0 | 16.4 | +9.9 | — |
|  | 10.0 | 28.8 | +22.3 | — |
| 0.56 | 0 | 15.3 | +8.8 | — |
|  | 1.0 | 30.1 | +23.6* | +18.7 |
|  | 10.0 | 24.7 | +18.2 | +31.1 |
| 1.78 | 0 | 24.6 | +18.1 | — |
|  | 1.0 | 37.8 | +31.3* | +28.0 |
|  | 10.0 | 27.3 | +20.8 | +40.4 |

**Much greater than additive; pronounced synergism

EXAMPLE 4

Activity of (7S,9S)-2-(2-Pyrimidyl)-7-(succinimidomethyl)perhydro-1H-pyrido[1,2-a]-pyrazine (CP-X) and Idazoxan (IDZ), Alone and in Combination, in the Vogel Anticonflict Test in Rats According to the method detailed in the specification above, DPAT and 1-PP were tested in the Vogel anticonflict test with results as follows:

| Dose of IDZ SC, 60 min. prior to test (mg/kg) | Dose of CP-X ip, 15 min. prior to test (mg/kg) | Number of Drinks over 10 min. Test Period | Observed Increase in No. of Drinks over Control | Calculated Increase in No. of Drinks if Additive |
|---|---|---|---|---|
| Test A |  |  |  |  |
| 0 | 0 | 6.6 | — | — |
|  | 1.0 | 11.3 | +4.7 | — |
|  | 5.6 | 21.3 | +14.7 | — |
| 0.56 | 0 | 10.0 | +3.4 | — |
|  | 1.0 | 30.3 | +23.7* | +8.1 |
|  | 5.6 | 45.4 | +38.8** | +18.1 |
| 1.78 | 0 | 14.9 | +8.3 | — |
|  | 1.0 | 28.0 | +21.4* | +13.0 |
|  | 5.6 | 39.3 | +32.7* | +23.0 |
| Test B |  |  |  |  |
| 0 | 0 | 8.4 | — | — |
|  | 1.0 | 9.6 | +1.2 | — |
|  | 5.6 | 34.0 | +25.6 | — |
| 0.56 | 0 | 18.6 | +10.2 | — |
|  | 1.0 | 28.0 | +19.6* | +11.4 |
|  | 5.6 | 89.0 | +80.6** | +35.8 |
| 1.78 | 0 | 19.1 | +10.7 | — |
|  | 1.0 | 24.1 | +15.7* | +11.9 |
|  | 5.6 | 76.9 | +68.5** | +36.3 |
| Test C |  |  |  |  |
| 0 | 0 | 6.9 | — | — |
|  | 1.0 | 13.1 | +6.2 | — |
|  | 5.6 | 42.0 | +35.1 | — |
| 0.1 | 0 | 9.4 | +2.5 | — |
|  | 1.0 | 18.6 | +11.7* | +8.7 |
|  | 5.6 | 45.5 | +38.6 | +37.6 |
| 0.56 | 0 | 12.1 | +5.2 | — |
|  | 1.0 | 31.1 | +24.2** | +11.4 |
|  | 5.6 | 35.0 | +28.1 | +40.3 |

*Greater than additive; synergism indicated
**Much greater than additive; pronounced synergism

EXAMPLE 5

Activity of Gepirone (GEP) and Idazoxan (IDZ), Alone and In Combination, in the Vogel Anticonflict Test in Rats According to the method detailed above, GEP and IDZ were tested in the Vogel Anticonflict test with results as follows:

| Dose of IDZ SC, 60 min. prior to test (mg/kg) | Dose of GEP ip, 15 min. prior to test (mg/kg) | Number of Drinks over 10 min. Test Period | Observed Increase in No. of Drinks over Control | Calculated Increase in No. of Drinks if Additive |
|---|---|---|---|---|
| 0 | 0 | 5.9 | — | — |
|  | 1.0 | 10.0 | +4.1 | — |
|  | 10.0 | 22.1 | +16.2 | — |
| 0.56 | 0 | 9.8 | +3.9 | — |
|  | 1.0 | 16.3 | +10.4* | +8.0 |
|  | 10.0 | 37.4 | +31.5** | +20.1 |
| 1.78 | 0 | 12.1 | +6.2 | — |
|  | 1.0 | 45.6 | +39.7* | +10.3 |

-continued

| Dose of IDZ SC, 60 min. prior to test (mg/kg) | Dose of GEP ip, 15 min. prior to test (mg/kg) | Number of Drinks over 10 min. Test Period | Observed Increase in No. of Drinks over Control | Calculated Increase in No. of Drinks if Additive |
|---|---|---|---|---|
| | 10.0 | 47.0 | +41.1** | +22.4 |

*Greater than additive; synergism indicated
**Much greater than additive; pronounced synergism

EXAMPLE 6

Activity of Ipsapirone (IPS) and Idazoxan (IDZ), Alone and in Combination, in the Vogel Anticonflict Test According to the method detailed in the specification above, IPS and IDZ were tested in the Vogel anticonflict test with results as follows:

| Dose of IDZ SC, 60 min. prior to test (mg/kg) | Dose of IPS ip, 15 min. prior to test (mg/kg) | Number of Drinks over 10 min. Test Period | Observed Increase in No. of Drinks over Control | Calculated Increase in No. of Drinks if Additive |
|---|---|---|---|---|
| Test A | | | | |
| 0 | 0 | 6.2 | — | — |
| | 3.2 | 6.1 | −0.1 | — |
| | 10.0 | 10.8 | +4.6 | — |
| 0.56 | 0 | 8.5 | +2.3 | — |
| | 3.2 | 9.6 | +3.4* | +2.2 |
| | 10.0 | 31.4 | +25.2** | +6.9 |
| 1.78 | 0 | 14.0 | +7.8 | — |
| | 3.2 | 17.9 | +11.7* | +7.7 |
| | 10.0 | 29.4 | +23.2** | +12.4 |
| Test B | | | | |
| 0 | 0 | 5.0 | — | — |
| | 1.0 | 8.8 | +3.8 | — |
| | 10.0 | 10.3 | +5.3 | — |
| 0.56 | 0 | 15.9 | +10.9 | — |
| | 1.0 | 11.4 | +6.4 | +14.7 |
| | 10.0 | 15.3 | +10.3 | +16.2 |
| 1.78 | 0 | 13.4 | +8.4 | — |
| | 1.0 | 11.9 | +6.9 | +12.2 |
| | 10.0 | 26.7 | +21.7** | +13.7 |
| Test C | | | | |
| 0 | 0 | 3.3 | — | — |
| | 1.0 | 5.9 | +2.6 | — |
| | 10.0 | 7.9 | +4.4 | — |
| 0.56 | 0 | 6.4 | +3.1 | — |
| | 1.0 | 19.9 | +16.6** | +5.7 |
| | 10.0 | 16.4 | +13.1* | +7.5 |
| 1.78 | 0 | 10.6 | +7.3 | — |
| | 1.0 | 14.8 | +11.5* | +9.9 |
| | 10.0 | 19.3 | +16.0** | +11.7 |
| Test D | | | | |
| 0 | 0 | 8.3 | — | — |
| | 0.32 | 6.2 | −2.1 | — |
| | 1.0 | 6.4 | −1.9 | — |
| 0.32 | 0 | 11.0 | +2.7 | — |
| | 0.32 | 21.3 | +13.0** | +0.6 |
| | 1.0 | 17.0 | +8.7** | +0.8 |
| 1.0 | 0 | 13.1 | +4.8 | — |
| | 0.32 | 24.0 | +15.7** | +2.7 |

| Dose of IDZ SC, 60 min. prior to test (mg/kg) | Dose of IPS ip, 15 min. prior to test (mg/kg) | Number of Drinks over 10 min. Test Period | Observed Increase in No. of Drinks over Control | Calculated Increase in No. of Drinks if Additive |
|---|---|---|---|---|
| | 1.0 | 26.9 | +18.6** | +2.9 |

*Greater than additive; synergism indicated
**Much greater than additive; pronounced synergism

EXAMPLE 7

Activity of Chlordiazepoxide (LIB) and Idazoxan (IDZ), Alone and in Combination, in the Vogel Anticonflict Test According to the method detailed above, LIB and IDZ were tested in the Vogel anticonflict test with results as follows:

| Dose of IDZ SC, 60 min. prior to test (mg/kg) | Dose of LIB ip, 15 min. prior to test (mg/kg) | Number of Drinks over 10 min. Test Period | Observed Increase in No. of Drinks over Control | Calculated Increase in No. of Drinks if Additive |
|---|---|---|---|---|
| Test A | | | | |
| 0 | 0 | 12.8 | — | — |
| | 1.0 | 7.5 | −5.3 | — |
| | 10.0 | 13.7 | +0.9 | — |
| 0.56 | 0 | 16.6 | +3.8 | — |
| | 1.0 | 20.3 | +7.5* | −1.5 |
| | 10.0 | 73.0 | +60.2** | +4.7 |
| 1.78 | 0 | 17.3 | +4.5 | — |
| | 1.0 | 13.3 | +0.5 | −0.8 |
| | 10.0 | 69.3 | +56.5** | +5.4 |
| Test B | | | | |
| 0 | 0 | 6.9 | — | — |
| | 1.0 | 7.3 | +0.4 | — |
| | 10.0 | 18.8 | +11.9 | — |
| 0.56 | 0 | 12.4 | +5.5 | — |
| | 1.0 | 11.9 | +5.0 | +5.9 |
| | 10.0 | 78.5 | +71.6** | +17.4 |
| 1.78 | 0 | 16.5 | +9.6 | — |
| | 1.0 | 32.6 | +25.7** | +10.0 |
| | 10.0 | 113.9 | +107** | +21.5 |

*Greater than additive; synergism indicated
**Much greater than additive; pronounced synergism

I claim:

1. A synergistic anxiolytic combination comprising 8-hydroxy-2-(dipropylamino)-1,2,3,4-tetrahydronaphthalene and 1-(2-pyrimidyl)piperazine, wherein the weight ratio of 8-hydroxy-2-(dipropylamino)-1,2,3,4-tetrahydronaphthalene to 1-(2-pyrimidyl)piperazine is in the range from 1:1 to 1:10.

2. A combination according to claim 1, wherein the weight ratio is 1:10.

3. A pharmaceutical composition comprising an antianxiety-effective amount of a synergistic combination according to claim 1 and a pharmaceutically-acceptable carrier.

4. A method of treating anxiety in a mammal which comprises administering to said mammal an antianxiety-effective amount of a synergistic combination according to claim 1.

5. A method according to claim 4, wherein the combination is administered orally.

* * * * *